United States Patent [19]

Kronenthal

[11] Patent Number: 4,612,923
[45] Date of Patent: Sep. 23, 1986

[54] GLASS-FILLED, ABSORBABLE SURGICAL DEVICES

[75] Inventor: Richard L. Kronenthal, Fair Lawn, N.J.

[73] Assignee: Ethicon, Inc., Somerville, N.J.

[21] Appl. No.: 557,038

[22] Filed: Dec. 1, 1983

[51] Int. Cl.[4] ................................. A61F 5/04
[52] U.S. Cl. ......................... 128/92 R; 128/92 G; 128/325
[58] Field of Search ............... 128/92 R, 346, 92 E, 128/303 R, 92 G, 325; 3/1.9

[56] References Cited

U.S. PATENT DOCUMENTS

| | | | |
|---|---|---|---|
| 3,787,900 | 1/1974 | McGee | 3/1.9 |
| 3,992,725 | 11/1976 | Homsy | 3/1.9 |
| 4,097,935 | 7/1978 | Jarcho | 3/1.9 |
| 4,131,597 | 12/1978 | Blüethgen et al. | 3/1.9 |
| 4,195,366 | 4/1980 | Jarcho et al. | 3/1.9 |
| 4,350,532 | 9/1982 | Randklev | 3/1.9 |
| 4,366,253 | 12/1982 | Yagi | 3/1.9 |
| 4,414,967 | 11/1983 | Shapiro | 128/92 E |
| 4,418,694 | 12/1983 | Beroff et al. | 128/346 |
| 4,437,192 | 3/1984 | Fujiu | 3/1.9 |
| 4,446,579 | 5/1984 | Inamori et al. | 3/1.9 |

Primary Examiner—Robert Peshock
Assistant Examiner—C. W. Shedd
Attorney, Agent, or Firm—Charles J. Metz

[57] ABSTRACT

A surgical device fabricated from a synthetic absorbable polymer containing an absorbable glass filler.

9 Claims, 3 Drawing Figures

GLASS-FILLED, ABSORBABLE SURGICAL DEVICES

The invention relates to surgical devices such as staples and ligating clips fabricated from absorbable polymers containing an absorbable glass reinforcing filler.

BACKGROUND OF THE INVENTION

Surgical devices such as staples made from stainless steel are becoming more frequently used in the medical profession as substitutes for and/or complements to surgical sutures and ligatures. In some surgical procedures, the staples are used internally. For instance, in a bowel resection, single or multiple rows of staples are deployed circumferentially around each bowel end that is to be rejoined. Staples thus employed are not removed, but are left inside the patient. While the body has ways of isolating such foreign objects that are left inside a patient so that the staples are not detrimental, surgeons would prefer to use absorbable staples that would eventually disappear from the body after their function during wound healing has been served.

It has been proposed to produce staples from synthetic absorbable polymers. For instance,, many patents that relate to synthetic absorbable polymers disclose surgical staples as one of many proposed uses. However, thus far, surgical staples made from synthetic absorbable polymers have not yet been used in the medical profession because the polymers have yet to achieve the requisite combination of properties. A staple made from an absorbable polymer must have sufficient stiffness to penetrate tissue, it must retain sufficient strength to perform its function during the wound healing process, and then eventually be absorbed by the body. It has proven to be especially difficult to achieve this necessary combination of properties.

Unlike the case with staples, surgical ligating clips made from synthetic absorbable polymers are being used in the medical profession. Such clips ordinarily comprise two legs joined by a hinge, with locking means at the ends of the legs that are opposite the hinge ends. The beam stiffness of the two legs is important for maintaining tight closure of the clip. By increasing the stiffness of the polymer from which the clip is made, either the beam stiffness can be increased or the size of the legs can be reduced.

This invention provides a means for improving the stiffness and other key mechanical properties of synthetic absorbable polymers, and therefore enhances the utility of staples, ligating clips, and other surgical devices made from such polymers.

BRIEF SUMMARY OF THE INVENTION

The invention provides a surgical device such as a staple or a ligating clip comprising a synthetic absorbable polymer containing an absorbable glass filler.

THE PRIOR ART

The preparation of soluble glasses based upon $P_2O_5$ is known. For instance, such glasses are disclosed by Drake and his co-workers in U.S. Pat. Nos. 4,123,248, 4,148,623, and 4,350,675, in British Pat. Nos. 1,512,637, 1,542,414, and 1,565,906 and in published British Patent Application Nos. 2,057,420, 2,077,586, 2,079,152, and 2,081,703 and by Roberts in U.S. Pat. Nos. 3,897,236, 3,930,833, and 3,958,973.

The addition of fillers to synthetic absorbable polymers is described, for instance, in European Patent Application No. 0050215, French Pat. No. 2,364,644, German Pat. No. 27 42 128, British Pat. No. 1,593,288, and U.S. Pat. No. 4,279,249.

DETAILED DESCRIPTION OF THE INVENTION

Figure 1:
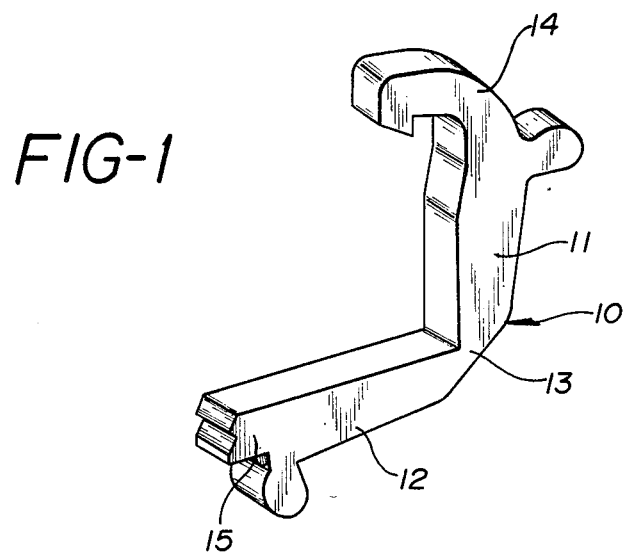
FIG. 1 is an enlarged perspective view of a ligating clip in accordance with the invention.

The polymers employed in this invention are the synthetic absorbable polymers. Such polymers include lactide and glycolide homopolymers and block and random copolymers such as are disclosed by Wasserman et al. in U.S. Pat. No. 3,839,297, Glick et al. in U.S. Pat. Nos. 3,297,033 and 3,620,218, and Schneider in U.S. Pat. No. 3,636,956, and poly-1,4-dioxanone homopolymers and copolymers, such as are disclosed by Doddi et al. in U.S. Pat. No. 4,052,988.

The absorbable glasses employed in the invention are those based upon $P_2O_5$ as the network former, and which contain at least one alkali or alkaline earth metal oxide such as sodium oxide, potassium oxide, calcium oxide, magnesium oxide, and the like. The following table displays typical proportions of the various oxides that can be present in the glass:

TABLE I

| Component | Proportions, Mole % |
|---|---|
| $Na_2O$ | 0–50 |
| $K_2O$ | 0–50 |
| CaO | 0–30 |
| MgO | 0–30 |
| $P_2O_5$ | 30–70 |

Although the custom in the art is to refer to the constituents in the form of the oxides, the oxides per se need not be used in producing the glass. For instance, the following materials can be used:

$(NH_4)_3PO_4$
$(NH_4)_2HPO_4$
$NaH_2PO_4$
$KH_2PO_4$
$CaCO_3$
$Ca(H_2PO_4)_2$
$MgCO_3$
$P_2O_5$
$MgHPO_4$
$Zn_3(PO_4)_2$
MgO

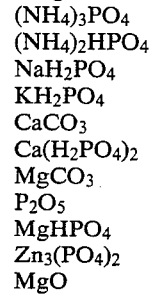

As a general rule, the solubility rate (in aqueous media) is increased by increasing the proportion of alkali metal oxides (i.e., $Na_2O$ and $K_2O$), and is decreased by increasing the proportion of alkaline earth metal oxides (CaO and MgO). Thus, within certain limits, the solubility rate of the glass can be varied. Other oxides can be added, in small amounts, if desired. For example, small amounts of $SiO_2$, $B_2O_3$, ZnO can be added for the purpose of retarding the dissolution rate for certain applications, or for enhancing processability.

The glasses are produced by fusing the ingredients in the desired proportions in a platinum or a dense alumina crucible. Typical fusion temperatures are 800° to 1100° C., and typical fusion times are about one to four hours. After fusion, the molten glass may be quenched, and then subjected to pulverizing to reduce the glass to a very fine particle size. The pulverizing of the glass can be done by known procedures such as air jet milling, ball milling, or the like. As a rule, the powders used are of very fine particle size, e.g., below 200 mesh and in some cases below 400 mesh (Tyler Standard Sieve Series). It is also within the scope of the invention to employ the glass in the form of low denier fibers (either staple fibers or continuous filaments), for instance, fibers having diameters of from about 2 to 10 microns and aspect ratios (length/diameter) of about 40 to 100. The fibers can be made by known methods such as melt spinning.

The proportion of glass filler in the polymer can vary from case to case, but will usually be within the range of from about 10 to about 60 weight per cent, based on the weight of the filled polymer. In any event, the exact proportion of glass filler is not narrowly critical. The glass is employed in an amount sufficient to increase the stiffness of the polymer, as indicated by an increase in Young's modulus.

The glass is incorporated in the polymer by conventional procedures for adding fillers to polymers. For instance, polymer pellets and glass powder or fibers, are intimately mixed in a blender, and the mixture is then compounded through an extruder. Injection or compression molding techniques can also be used. The glass can also be used in the form of continuous filaments, and rods comprising the continuous filament glass embedded in a matrix of synthetic absorbable polymer can be produced by the extrusion technique known as "pultrusion" wherein the polymer is continuously extruded around glass filaments that are pulled through the extruder nozzle. Such rods can be chopped or cut to any desired length, after the pultrusion operation.

Figure 2:
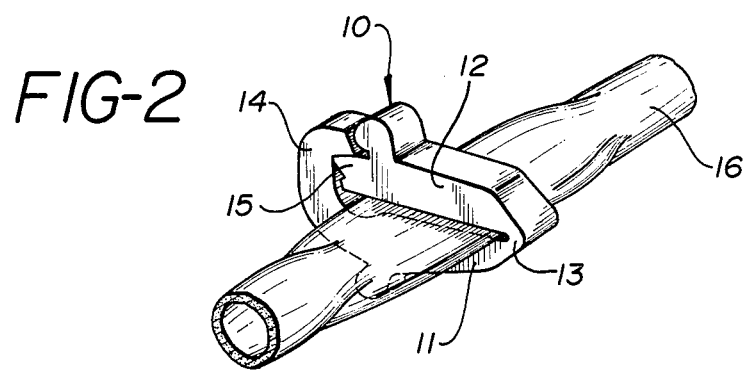
FIG. 2 is an enlarged perspective view showing the clip of FIG. 1 in place closing off a blood vessel.
Figure 3:
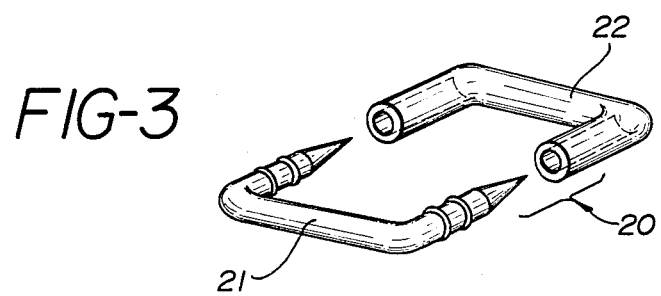
FIG. 3 is an enlarged perspective view of another sugical device in accordance with the invention.

Referring to the drawings, there are depicted certain specific types of surgical devices which may embody the principles of the invention. In FIG. 1, there is shown a ligating clip 10. This clip is used to ligate a blood vessel during various surgical procedures. The clip comprises two leg members 11 and 12 joined at their proximal end by a hinge section 13. The leg members latch or lock at their distal ends 14 and 15. In FIG. 2 there is shown the clip of FIG. 1 in its closed position closing off the lumen of a blood vessel 16. Another surgical device is shown in FIG. 3. This device is a 2-piece fastener 20 for closing wounds and the like. The fastener comprises a staple 21 and a receiver 22 for the staple.

Other medical devices which are contemplated within the invention are solid products such as orthopedic pins, clamps, screws and plates; clips, staples, hooks, buttons, and snaps; bone substitutes such as mandible prosthesis; needles; vascular implants, couplers or supports; and vertebral discs, as well as other similar devices.

It will be apparent that improving various strength properties, especially stiffness, will enhance the usefulness of the devices contemplated by this invention. For instance, when employing the fastener 20 of FIG. 3 to hold tissue, it is apparent that the staple portions 21 must hold a true course when penetrating tissue, in order for it to meet the receiver 22 properly. This invention provides a means for stiffening the staple 21, by increasing its rigidity or column strength, so that it will be less apt to deviate or be deflected from its desired course as it pierces tissue.

The ligating clip shown in FIGS. 1 and 2 has enhanced utility when made in accordance with the invention because the beam stiffness of the legs 12, 14 is increased, which thereby enhances the closure security.

By adjusting the absorption rate of the glass filler, as taught herein, the absorption rates of the surgical devices of the invention can be modified. For instance, in some cases it may be desirable to use a filler having a different absorption rate (usually faster) than the polymer matrix. For instance, tissue ingrowth into the device may be accelerated by using a glass that absorbs much more rapidly than the polymer matrix.

The following examples illustrate various aspects of the invention.

EXAMPLE 1

An alumina crucible was charged with 500 grams of $NaH_2PO_4 \cdot H_2O$ and heated in an electric furnace at about 800° C. for 3–4 hours, after which it was poured out onto a steel tray. Fibers are drawn from the molten glass by known procedures. After cooling sufficiently, the glass was broken up and collected in a jar. About 350 grams was recovered. Portions of this were pulverized in a porcelain jar mill.

EXAMPLE 2

An alumina crucible was charged with 210 grams of $NaH_2PO_4 \cdot H_2O$ and 90 grams of $CaH_4(PO_4)_2 \cdot H_2O$, and heated about ½ hour at 1000°–1300° C. in a gas fired air turbine. The melt was treated as in Example 1, above.

EXAMPLE 3

An alumina crucible was charged with 210 grams of $NaH_2PO_4 \cdot H_2O$ and 90 grams of zinc phosphate, and a glass was prepared as in Examples 1 & 2 above.

EXAMPLE 4

An alumina crucible was charged with 210 grams of sodium hexametaphosphate and 90 grams of monobasic (primary) magnesium phosphate, and a glass was prepared as in Examples 1, 2, 3, above.

EXAMPLE 5

A 325 mesh ground phosphate absorbable glass, such as described in Examples 1–4, is dry blended at a 20% by weight level with poly-dioxanone polymer and melt blended in a single screw extruder containing a 3½:1 compression ratio screw and mixing elements. The extrudate is quenched, pelletized and dried. The compounded pellets are then injection molded at 120° C. into ASTM dogbone test specimens, annealed at 85° C. for 16 hours, and tested in accordance with ASTM Test Method D638. Significant increase in Young's Modulus is noted while sufficient ultimate elongation remains to ensure ductility. Typical physical properties are as follows:

|  | Elong., % | Y.M., psi |
|---|---|---|
| Raw Control, 0% Phosphate Glass | 806 | 23,900 |
| Raw, 20% Phosphate Glass | 450 | 30,900 |
| Annealed Control, 0% Phosphate Glass | 776 | 26,900 |
| Annealed, 20% Phosphate Glass | 125 | 40,600 |

What is claimed is:

1. An absorbable surgical device comprising a synthetic absorbable polymer containing an absorbable glass reinforcing filler in an amount sufficient to increase the stiffness of said polymer.

2. The device of claim 1 wherein said glass is a phosphate glass.

3. The device of claim 2 wherein the glass also contains one or more oxides of sodium, potassium, calcium, and magnesium.

4. The device of claim 1 wherein said polymer is poly-1,4-dioxanone.

5. The device of claim 1 wherein said polymer is a homopolymer or copolymer of glycolide or lactide.

6. The device of claim 1, 2, 3, 4, or 5 in the form of a staple.

7. The device of claim 1, 2, 3, 4, or 5 in the form of a ligating clip.

8. The device of claim 1 wherein the glass reinforcing filler is in the form of a powder.

9. The device of claim 1 wherein the glass reinforcing filler is in fibrous form.

* * * * *